(12) United States Patent
Yoshida

(10) Patent No.: US 9,967,486 B2
(45) Date of Patent: May 8, 2018

(54) IMAGE PICKUP APPARATUS

(71) Applicant: OLYMPUS CORPORATION, Tokyo (JP)

(72) Inventor: Kazuhiro Yoshida, Nagano (JP)

(73) Assignee: OLYMPUS CORPORATION, Tokyo (JP)

(*) Notice: Subject to any disclaimer, the term of this patent is extended or adjusted under 35 U.S.C. 154(b) by 517 days.

(21) Appl. No.: 14/088,800

(22) Filed: Nov. 25, 2013

(65) Prior Publication Data

US 2014/0078280 A1    Mar. 20, 2014

Related U.S. Application Data

(63) Continuation of application No. PCT/JP2012/064289, filed on Jun. 1, 2012.

(30) Foreign Application Priority Data

Jun. 8, 2011   (JP) ................................. 2011-128619

(51) Int. Cl.
*H04N 5/369*   (2011.01)
*A61B 1/00*    (2006.01)
*A61B 1/05*    (2006.01)

(52) U.S. Cl.
CPC ......... *H04N 5/369* (2013.01); *A61B 1/00163* (2013.01); *A61B 1/051* (2013.01)

(58) Field of Classification Search
CPC ..... A61B 1/00163; A61B 1/051; H04N 5/369
(Continued)

(56) References Cited

U.S. PATENT DOCUMENTS 3,499,107 A * 3/1970 Edward .............. A61B 1/00165
250/227.2
4,622,954 A    11/1986 Arakawa et al.
(Continued)

FOREIGN PATENT DOCUMENTS

EP    1 661 506 A1    5/2006
JP    62-35314 U      3/1987
(Continued)

OTHER PUBLICATIONS

Extended Supplementary European Search Report dated Feb. 9, 2015 from related European Application No. 12 79 7267.7.
(Continued)

*Primary Examiner* — Andy Rao
*Assistant Examiner* — Zaihan Jiang
(74) *Attorney, Agent, or Firm* — Scully, Scott, Murphy & Presser, P.C.

(57) ABSTRACT

An image pickup apparatus includes: a solid-state image pickup device partitioned into a light-receiving portion region that generates an image pickup signal of an optical image, a circuit portion region that processes the image pickup signal and generates a driving signal, and a terminal portion region having terminals for inputting/outputting signals with an external apparatus; and an objective optical portion having an objective lens unit including a unit main body having an objective lens group for forming an optical image and a holding barrel where the unit main body is fixed, and a prism that guides the optical image that passes through the objective lens unit to the light-receiving portion region. The prism of the objective optical portion is disposed on the light-receiving portion region of the substrate, and the holding barrel of the objective lens unit is disposed on the circuit portion region.

9 Claims, 10 Drawing Sheets

(58) Field of Classification Search
USPC .......................................................... 348/76
See application file for complete search history.

(56) References Cited

U.S. PATENT DOCUMENTS

| | | | |
|---|---|---|---|
| 4,646,721 A | | 3/1987 | Arakawa |
| 4,682,219 A | | 7/1987 | Arakawa |
| 4,809,680 A | | 3/1989 | Yabe |
| 4,832,003 A | * | 5/1989 | Yabe ..................... A61B 1/051 348/65 |
| 6,319,196 B1 | | 11/2001 | Minami |
| 2006/0025651 A1 | | 2/2006 | Adler et al. |
| 2006/0028442 A1 | * | 2/2006 | Bynum ................ G06F 3/0317 345/157 |
| 2006/0132598 A1 | | 6/2006 | Minami et al. |
| 2008/0291543 A1 | * | 11/2008 | Nomura ............... G02B 15/177 359/676 |
| 2013/0317529 A1 | * | 11/2013 | Golden ............. A61B 10/0275 606/159 |

FOREIGN PATENT DOCUMENTS

| | | |
|---|---|---|
| JP | 63-177106 A | 7/1988 |
| JP | 10-033474 A | 2/1998 |
| JP | 2000-019427 A | 1/2000 |
| JP | 2002-136474 A | 5/2002 |
| JP | 2006-141884 A | 6/2006 |
| JP | 2008-118568 A | 5/2008 |
| JP | 2009-268639 A | 11/2009 |
| JP | 2009-288682 A | 12/2009 |
| JP | 2010-051538 A | 3/2010 |
| JP | 2010-069186 A | 4/2010 |

OTHER PUBLICATIONS

International Seach Report dated Jul. 10, 2012 issued in PCT/JP2012/064289.

\* cited by examiner

IMAGE PICKUP APPARATUS

CROSS REFERENCE TO RELATED APPLICATION

This application is a continuation application of PCT/JP2012/064289 filed on Jun. 1, 2012 and claims benefit of Japanese Application No. 2011-128619 filed in Japan on Jun. 8, 2011, the entire contents of which are incorporated herein by this reference.

BACKGROUND OF INVENTION

1. Field of the Invention

The present invention relates to an image pickup apparatus that is used in an optical apparatus.

2. Description of the Related Art

An endoscope that is one kind of optical apparatus includes an image pickup apparatus that is mounted at a distal end portion of an insertion portion. It is desirable for the image pickup apparatus to be miniaturized so as to make the diameter of the distal end portion of the insertion portion narrow.

For example, Japanese Patent Application Laid-Open Publication No. 2009-288682 discloses an ultra-small endoscope objective optical system having an image pickup face parallel arrangement structure. In FIG. 1(a) of Patent Literature 1, an image pickup apparatus is illustrated which bends an optical axis of an objective optical system at a right angle by means of a prism, and guides the optical axis to a solid-state image pickup device that is provided parallel to a longitudinal axis direction of an insertion portion.

The present invention has been conceived in view of the above-described circumstances, and an object of the present invention is to provide an image pickup apparatus that is easy to handle and in which the thickness of a solid-state image pickup device is made even thinner so that the diameter of an endoscope insertion portion can be narrowed.

SUMMARY OF THE INVENTION

An image pickup apparatus according to one aspect of the present invention includes: a solid-state image pickup device in which one surface of a substrate is partitioned into a light-receiving portion region in which a light-receiving portion is provided that generates an image pickup signal of a picked-up optical image of a subject, a circuit portion region in which a circuit portion is provided that performs signal processing on the image pickup signal generated by the light-receiving portion and generates a driving signal that drives the light-receiving portion, and a terminal portion region in which a plurality of terminals are provided that are used when inputting and outputting signals between the circuit portion and an external apparatus; and an objective optical portion having an objective lens unit including a unit main body equipped with an objective lens group for forming an optical image of the subject and a holding barrel in which the unit main body is fixedly installed, and a prism that bends an optical axis of the unit main body and guides the optical image that passes through the objective lens unit to the light-receiving portion of the solid-state image pickup device; wherein the prism of the objective optical portion is disposed on the light-receiving portion region of the substrate, and the holding barrel comprising the objective lens unit of the objective optical portion is disposed on the circuit portion region.

DETAILED DESCRIPTION OF THE PREFERRED EMBODIMENT(S)

Embodiments of the present invention are described hereunder with reference to the drawings.

A first embodiment of the present invention will now be described with reference to FIG. 1 to FIG. 3.

Figure 1:
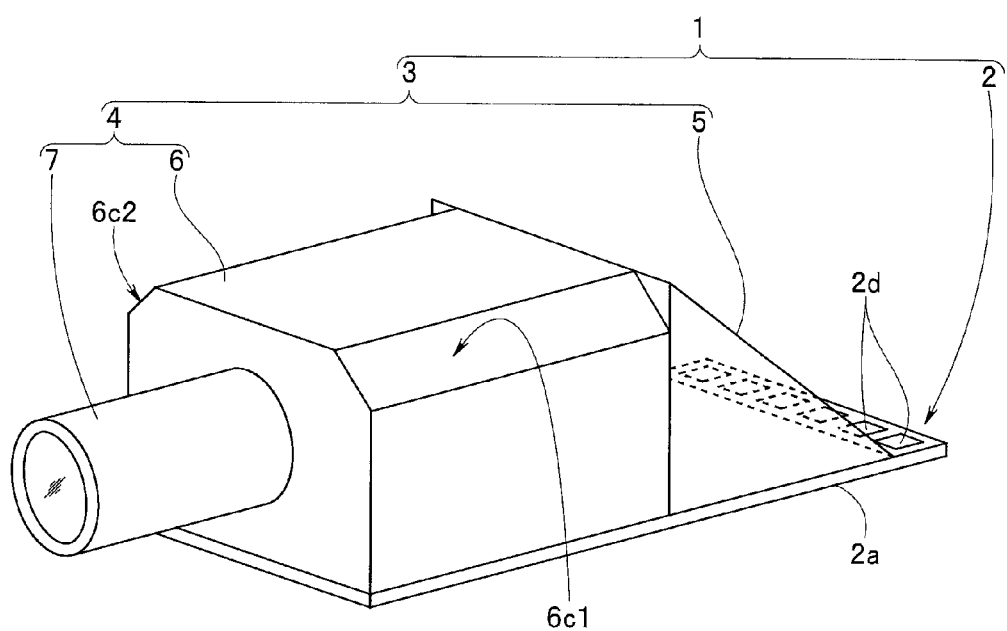
FIG. 1 is a view that illustrates an image pickup apparatus according to a first embodiment.

As shown in FIG. 1, an image pickup apparatus 1 of the present embodiment includes a solid-state image pickup device 2 and an objective optical portion 3. In the present embodiment, the objective optical portion 3 is integrally fixed to a front face that is one surface side of a substrate 2a, described later, that is included in the solid-state image pickup device 2.

Note that it is assumed in the following description that the term "one surface" represents the front face and the term "other surface" represents the rear face.

Figure 2:
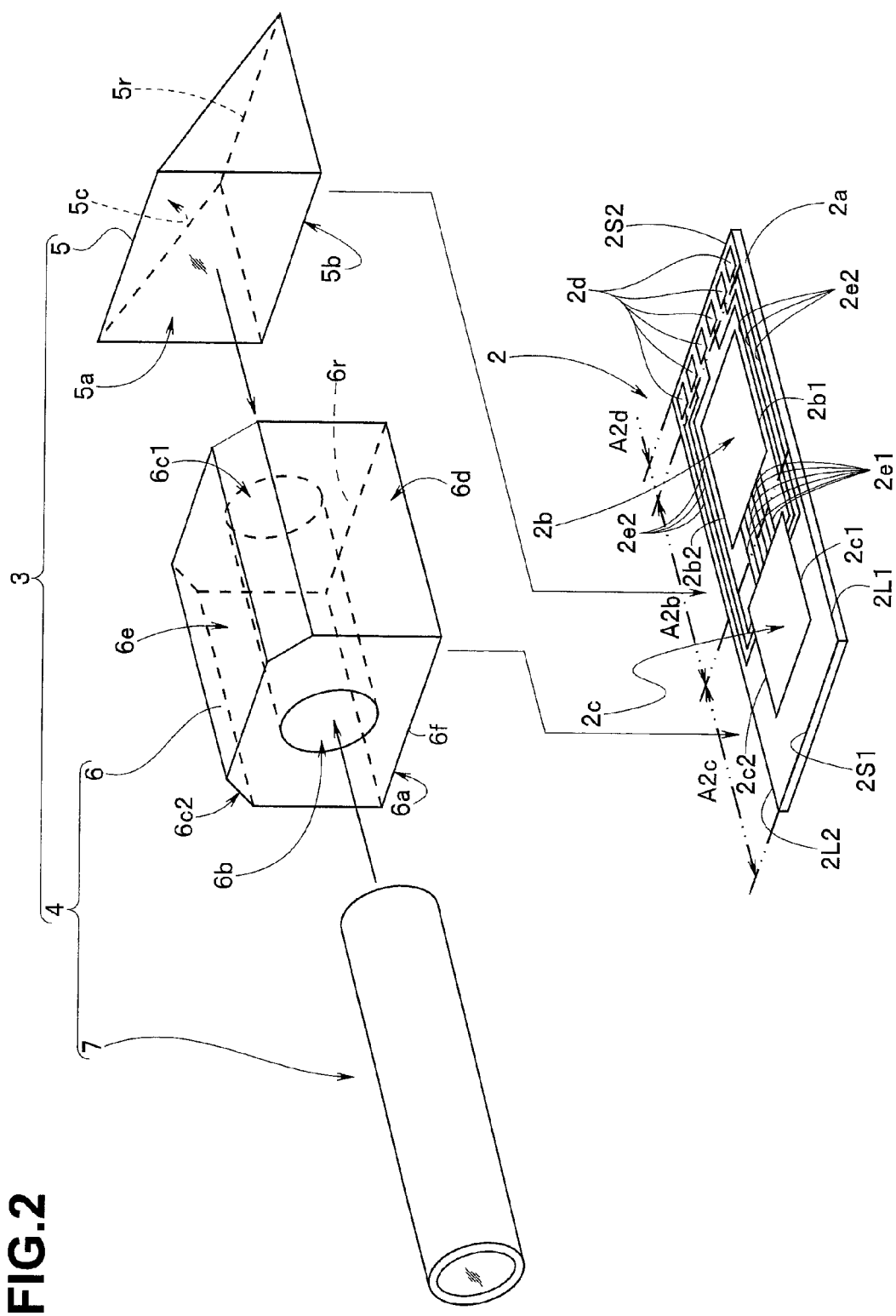
FIG. 2 is an exploded perspective view for describing the configuration of the image pickup apparatus according to the first embodiment.

As shown in FIG. 2, the solid-state image pickup device 2 includes a light-receiving portion 2b, a circuit portion 2c and a plurality of electrode pads 2*d* that are provided on the front face of the substrate 2*a* that has an approximately rectangular shape. The substrate 2*a* is made from silicon, for example.

In the present embodiment, the front face of the substrate 2*a* is partitioned into a circuit portion region A2*c*, a light-receiving portion region A2*b*, and a terminal portion region A2*d* in that order from the side of a first short edge 2S1 that is a distal end side of the substrate 2*a* towards a proximal end thereof.

The circuit portion 2*c* is provided at a predetermined position in the circuit portion region A2*c*. The light-receiving portion 2*b* is provided at a predetermined position in the light-receiving portion region A2*b*. Electrode pads 2*d* as a plurality of terminals are provided at predetermined positions in the terminal portion region A2*d*.

The plurality of electrode pads 2*d*, for example, are made of aluminum or the like, and are arrayed along a second short edge 2S2 that is the proximal end side of the substrate 2*a*, in a vicinity of the second short edge 2S2. The electrode pads 2*d* are used for inputting and outputting signals between the circuit portion 2*c* and a camera control unit (not shown) that is an external apparatus.

The light-receiving portion 2*b* picks up an optical image of a subject and generates an image pickup signal. The light-receiving portion 2*b* is formed in a predetermined size and shape by a plurality of photodiodes. The light-receiving portion 2*b* includes color filters (not shown) that are formed on the photodiodes, and microlenses (not shown) that are formed on the color filters.

The circuit portion 2*c* has a driving/signal processing circuit that performs signal processing on an image pickup signal generated by the light-receiving portion 2*b* and generates a driving signal that drives the light-receiving portion 2*b*. The driving/signal processing circuit includes, for example, a shift register, an output amplifier, an A/D converter, and a memory circuit.

The light-receiving portion 2*b* and the circuit portion 2*c* are electrically connected by a plurality of first wires 2*e*1. The circuit portion 2*c* and the respective electrode pads 2*d* are electrically connected by second wires 2*e*2.

The plurality of first wires 2*e*1 are parallel wires with respect to long edges 2L1 and 2L2 of the substrate 2*a*. The plurality of first wires 2*e*1 are formed so as to fit between a first edge 2*b*1 and a second edge 2*b*2 of the light-receiving portion 2*b* that are parallel to the long edges 2L1 and 2L2 of the substrate 2*a*, and so as to fit between a first edge 2*c*1 and a second edge 2*c*2 of the circuit portion 2*c* that are parallel to the long edges 2L1 and 2L2.

The second wires 2*e*2 are divided into two sets, namely a set of wires disposed on the long edge 2L1 side and a set of wires disposed on the long edge 2L2 side. One of the sets of the second wires 2*e*2 that are divided into two sets is formed so as to pass between the long edge 2L1 and the first edge 2*b*1 of the light-receiving portion 2*b* and thereafter connect to the corresponding electrode pad 2*d*. The other set of the second wires 2*e*2 is formed so as to pass between the long edge 2L2 and the second edge 2*b*2 of the light-receiving portion 2*b* and thereafter connect to the corresponding electrode pad 2*d*.

As shown in FIG. 1 and FIG. 2, the objective optical portion 3 includes an objective lens unit 4 and a prism 5. The objective lens unit 4 includes a holding barrel 6 and a unit main body 7.

Figure 3:
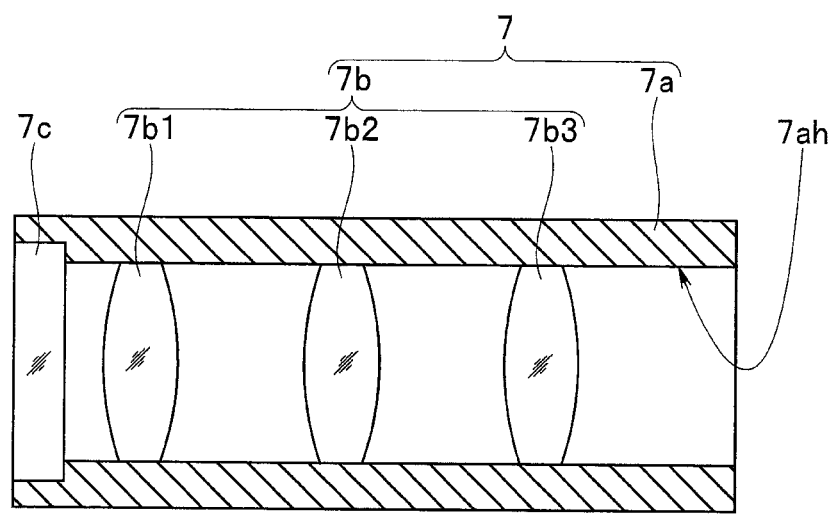
FIG. 3 is a longitudinal sectional view of a unit main body shown in FIG. 2.

As shown in FIG. 3, the unit main body 7 includes a lens barrel 7*a* and an objective lens group 7*b*.

The lens barrel 7*a* is, for example, pipe shaped, and has an axial through-hole 7*ah*. A plurality of optical lenses 7*b*1, 7*b*2 and 7*b*3 constituting the objective lens group 7*b* for forming an optical image of a subject are, for example, fixed by adhesion at predetermined positions inside the axial through-hole 7*ah* of the lens barrel 7*a*.

Note that the number of optical lenses constituting the objective lens group 7*b* is not limited to three, and may be more or less than three. Further, reference character 7*c* denotes a lens cover.

The holding barrel 6 is, for example, a rectangular parallelepiped shape as shown in FIG. 2, and is made of a light blocking material. The term "light blocking material" refers to, for example, metal or a resinous material that includes a light blocking substance such as carbon particles or a pigment. The holding barrel 6 has an installation face 6*a* that is disposed on the circuit portion region A2*c* on the front face of the substrate 2*a*. A through-hole 6*b* that has a central axis parallel to the longitudinal axis direction and into which the lens barrel 7*a* is inserted is formed in the holding barrel 6. Note that reference character 6*d* denotes a side face and reference character 6*e* denotes a top face.

The width dimension of the installation face 6*a* is the same dimension as the short edges 2S1 and 2S2 of the substrate 2*a*. The length dimension of the holding barrel 6 is set so that, in a state in which a distal end edge 6*f* of the installation face 6*a* is placed in line with the first short edge 2S1 of the substrate 2*a*, a proximal end edge 6*r* of the installation face 6*a* intersects with a predetermined position on the substrate 2*a*, more specifically, for example, a midway part of the plurality of first wires 2*e*1.

Reference characters 6*c*1 and 6*c*2 denote chamfered portions that constitute a part of the side faces 6*d*. In the drawings, the chamfered portions 6*c*1 and 6*c*2 are each a so-called C surface that is constituted by a flat surface. However, the chamfered portions 6*c*1 and 6*c*2 are not limited to a C surface, and may be a so-called R surface that is constituted by a curved surface. The holding barrel 6 may also be constructed without providing the chamfered portions 6*c*1 and 6*c*2.

The prism 5 is, for example, made of glass and, as shown in FIG. 2, includes an incidence surface 5*a*, an exit surface 5*b*, and a reflection surface 5*c*. The incidence surface 5*a* is disposed at the proximal end face of the holding barrel 6. The exit surface 5*b* is disposed on the light-receiving portion region A2*b* on the front face of the substrate 2*a* and covers the light-receiving portion 2*b*. The prism 5 causes an optical image that passes through the objective lens unit 4 and is incident from the incidence surface 5*a* to bend at a right angle, and guides the optical image to the light-receiving portion 2*b* of the solid-state image pickup device 2.

The width dimension of the prism 5 is the same dimension as the short edges 2S1 and 2S2 of the substrate 2*a*, similarly to the width dimension of the installation face 6*a* of the holding barrel 6. The length dimension of the prism 5 is set so that, in a state in which the incidence surface 5*a* is disposed at the proximal end face of the holding barrel 6, a proximal end edge 5*r* constituting the exit surface 5*b* and the reflection surface 5*c* is disposed at a predetermined position on the substrate 2*a*. As a result, the electrode pads 2*d* are exposed to an outside in a predetermined state.

In the present embodiment, the installation face 6*a* of the holding barrel 6 is disposed on the circuit portion region A2*c* on the front face of the substrate 2*a* and, for example, is adhesively fixed in an integral manner to the substrate 2*a* by means of a thermosetting adhesive or the like. As a result, the circuit portion region A2c of the substrate 2a is supported by the holding barrel 6.

The exit surface 5b of the prism 5 is disposed on the light-receiving portion region A2b on the front face of the substrate 2a, and, for example, is adhesively fixed in an integral manner to the substrate 2a by means of an ultraviolet-curing adhesive or the like. As a result, the light-receiving portion region A2b of the substrate 2a is supported by the prism 5. It is desirable that an adhesive used to adhere the prism 5 and the substrate 2a together has a transmittance of 90% or more in a wavelength region of light used to pick up images.

As shown in FIG. 1, the electrode pads 2d provided on the front face of the substrate 2a that are in an exposed state to the outside are electrically connected to respectively corresponding signal wires (not shown).

One example of a procedure for assembling the image pickup apparatus 1 will now be described.

When assembling the image pickup apparatus 1, a worker prepares the solid-state image pickup device 2, the prism 5, the holding barrel 6, and the unit main body 7 and the like.

Next, for example, the worker adhesively fixes the installation face 6a of the holding barrel 6 to the circuit portion region A2c on the substrate 2a of the solid-state image pickup device 2.

Subsequently, the worker disposes the incidence surface of the prism 5 at the proximal end face of the holding barrel 6, and adhesively fixes the exit surface 5b of the prism 5 to the thick portion region A2c on the substrate 2a of the solid-state image pickup device 2. As a result, the electrode pads 2d are in an exposed state on the substrate 2a.

Next, the worker electrically connects unshown signal wires to the plurality of electrode pads 2d. Thereafter, the worker inserts the unit main body 7 into the through-hole 6b of the holding barrel 6. The worker then moves the unit main body 7 back and forth in a longitudinal direction of the holding barrel 6 to perform focusing adjustment. After completing the focusing adjustment, the worker integrally fixes the unit main body 7 to the holding barrel 6 by adhesive bonding or the like.

As a result, the image pickup apparatus 1 shown in FIG. 1 is constructed.

Note that the assembly procedure is not limited to the sequence described above, and can be appropriately changed in consideration of workability.

Thus, the image pickup apparatus 1 is constructed by fixing the holding barrel 6 and the prism 5 at predetermined positions on the substrate 2a constituting the solid-state image pickup device 2, and exposing the plurality of electrode pads 2d that are arrayed in the terminal portion region A2d.

According to this configuration, regions other than the terminal portion region A2d of the substrate 2a constituting the solid-state image pickup device 2 are supported by the holding barrel 6 and the prism 5. Accordingly, the occurrence of a defect that a crack or breakage occurs in the solid-state image pickup device 2 can be significantly reduced. Consequently, the thickness of the solid-state image pickup device 2 can be decreased to reduce the size of the image pickup apparatus 1. Further, since handling of the small-size image pickup apparatus 1 can be performed with ease, the workability can be enhanced and the yield can be improved.

A second embodiment of the present invention will now be described referring to FIG. 4 to FIG. 9.

Figure 4:
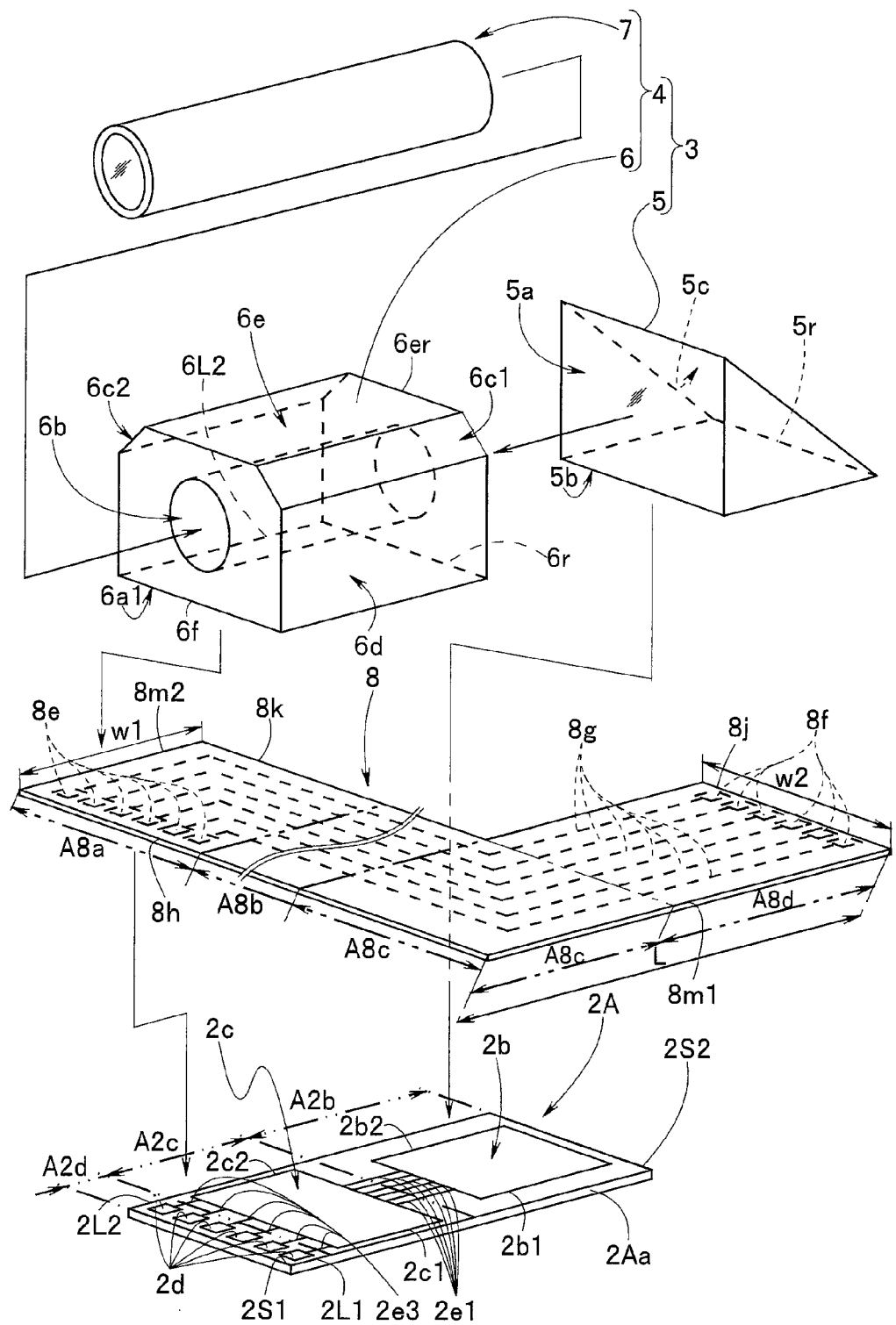
FIG. 4 is an exploded perspective view for describing the configuration of an image pickup apparatus according to a second embodiment.
Figure 5:
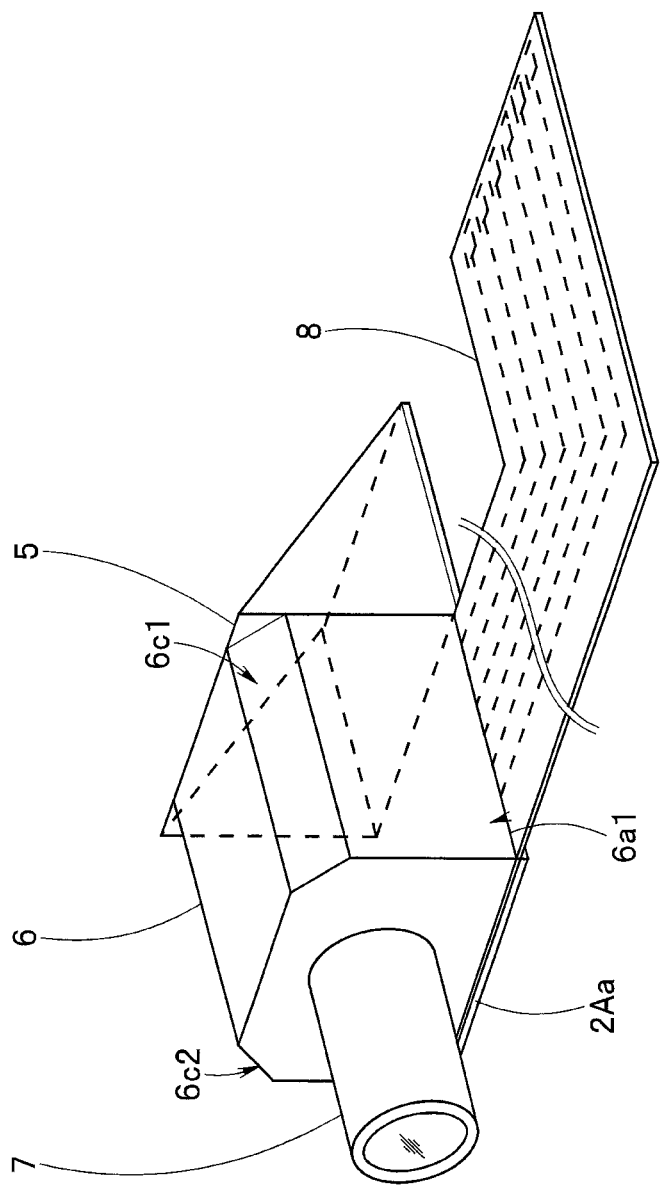
FIG. 5 is a view for describing a state in which, in the image pickup apparatus according to the second embodiment, a flexible substrate, a holding barrel, and a prism are mounted on a front face of a substrate constituting a solid-state image pickup device.
Figure 6:
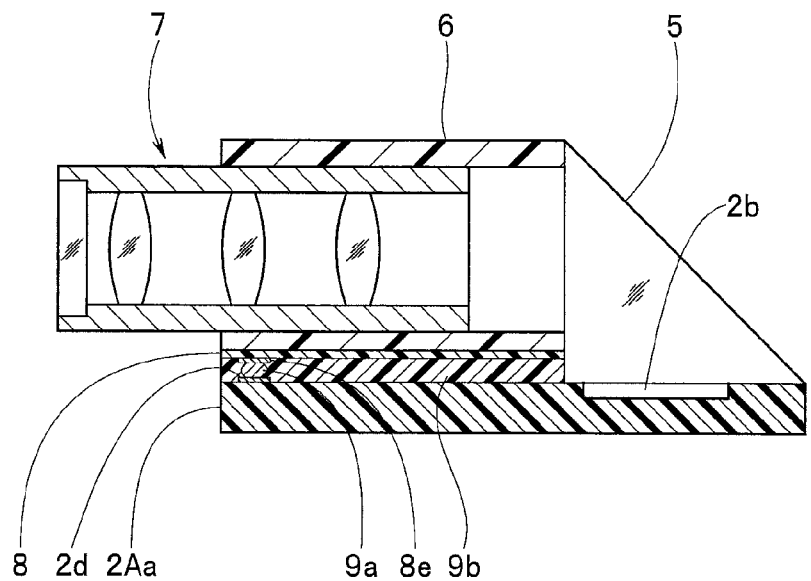
FIG. 6 is a view for describing, with respect to the image pickup apparatus according to the second embodiment, a connection relationship between electrode pads and pad connection electrodes in a state in which the flexible substrate, the holding barrel, and the prism are mounted on the front face of the substrate constituting the solid-state image pickup device.
Figure 7:
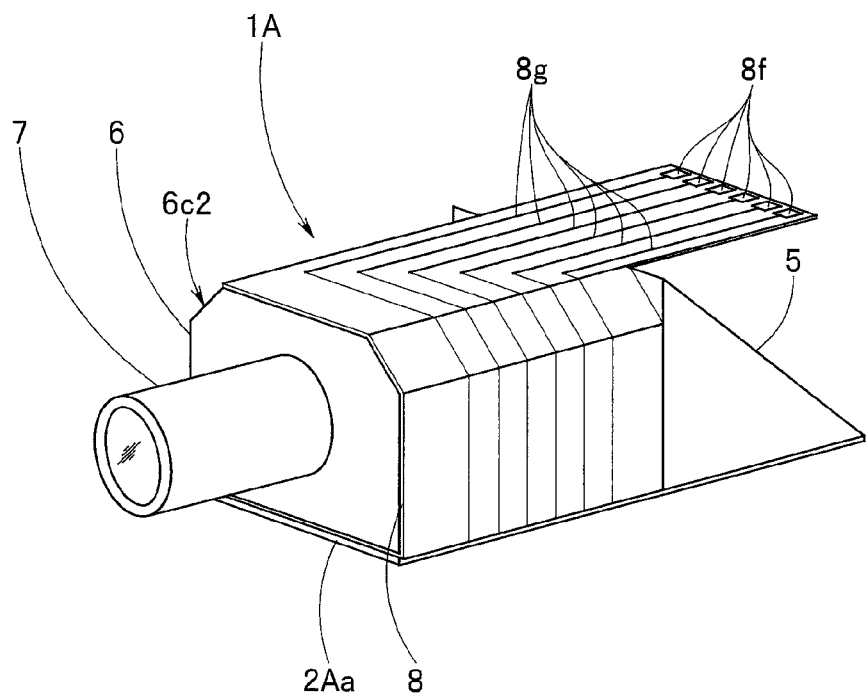
FIG. 7 is a view illustrating the image pickup apparatus according to the second embodiment.
Figure 8:
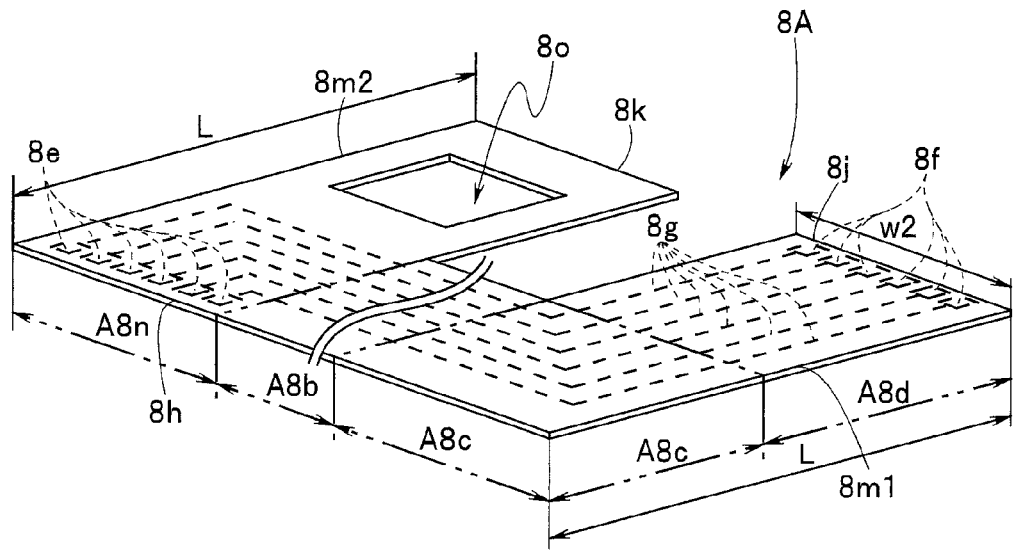
FIG. 8 is a view for describing another configuration example of the flexible substrate.
Figure 9:
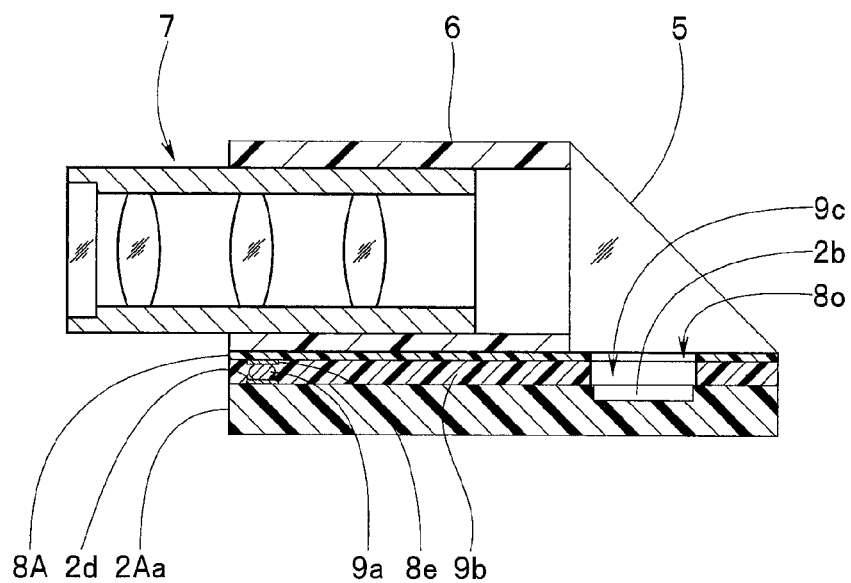
FIG. 9 is a view for describing the relationship between the prism and a light-receiving portion in a state in which the flexible substrate shown in FIG. 8, the holding barrel, and the prism are mounted on a front face of the solid-state image pickup device.

FIG. 4 is an exploded perspective view for describing the configuration of an image pickup apparatus according to the second embodiment. FIG. 5 is a view for describing a state in which, in the image pickup apparatus according to the second embodiment, a flexible substrate, a holding barrel, and a prism are mounted on a front face of a substrate constituting a solid-state image pickup device. FIG. 6 is a view that illustrates, with respect to the image pickup apparatus according to the second embodiment, a connection relationship between electrode pads and pad connection electrodes in a state in which the flexible substrate, the holding barrel, and the prism are mounted on the front face of the substrate constituting the solid-state image pickup device. FIG. 7 is a view illustrating the image pickup apparatus according to the second embodiment. FIG. 8 is a view for describing another configuration example of the flexible substrate. FIG. 9 is a view for describing the relationship between the prism and a light-receiving portion in a state in which the flexible substrate shown in FIG. 8, the holding barrel, and the prism are mounted on a front face of the solid-state image pickup device.

Note that in the following description of the second embodiment, components that are the same as in the foregoing first embodiment are denoted by the same reference characters and a description of such components is omitted.

An image pickup apparatus 1A of the present embodiment includes, as shown in FIG. 4, a solid-state image pickup device 2A, the objective optical portion 3, and a flexible substrate 8. As shown in FIG. 5, at least one section of the flexible substrate 8 is disposed between a front face of a substrate 2Aa and an installation face 6a1 of the holding barrel 6.

As shown in FIG. 4, similarly to the first embodiment, the solid-state image pickup device 2A of the present embodiment includes the light-receiving portion 2b, the circuit portion 2c, and the plurality of electrode pads 2d that are provided on the front face of the substrate 2Aa that has an approximately rectangular shape.

In the present embodiment, the order in which the respective regions are arranged from the first short edge 2S1 side that is a distal end side of the substrate 2Aa is different from the first embodiment. That is, in the present embodiment, the terminal portion region A2d, the circuit portion region A2c, and the light-receiving portion region A2b are provided in that order from the first short edge 2S1 side. As a result, in the present embodiment, the plurality of electrode pads 2d are arrayed along the first short edge 2S1 of the substrate 2Aa, in the vicinity of the first short edge 2S1.

In the present embodiment, the respective electrode pads 2d and the circuit portion 2c are electrically connected by a plurality of third wires 2e3 that are parallel to the long edges 2L1 and 2L2 of the substrate 2Aa, similarly to the first wires 2e1. The third wires 2e3 are formed so as to fit between the first edge 2c1 and the second edge 2c2 of the circuit portion 2c that are parallel to the long edges 2L1 and 2L2 of the substrate 2Aa.

The flexible substrate 8, for example, is made of a polyimide and is formed in an L shape. A front face that is one surface of the flexible substrate 8 is partitioned into an installation face region A8a, a side face region A8b, a top face region A8c, and a connection region A8d. The installation face 6a1 of the holding barrel 6 is disposed and fixed on the installation face region A8a. The side face region A8b is disposed on and fixed to the side face 6d and the chamfered portion 6c1 of the holding barrel 6. The top face region A8c is disposed and fixed on the top face 6e of the holding barrel 6. The connection region A8d is disposed so as to further protrude to the proximal end side from a proximal end edge 6er of the holding barrel 6.

A plurality of pad connection electrodes 8e, a plurality of signal-wire connection electrodes 8f, and a plurality of wires 8g are provided at predetermined positions on a rear face that is the other surface of the flexible substrate 8. The plurality of pad connection electrodes 8e are first electrodes that are electrically connected with the plurality of electrode pads 2d disposed in the terminal portion region A2d of the substrate 2Aa. The plurality of pad connection electrodes 8e are arrayed on a rear face of the installation face region A8a along a distal end edge 8h constituting the installation face region A8a, in a vicinity of the distal end edge 8h.

On the other hand, the plurality of signal-wire connection electrodes 8f are second electrodes to which corresponding signal wires (not shown) are electrically connected. The plurality of signal-wire connection electrodes 8f are arrayed on the rear face of the connection region A8d along a proximal end edge 8j constituting the connection region A8d, in a vicinity of the proximal end edge 8j.

The plurality of pad connection electrodes 8e and the plurality of signal-wire connection electrodes 8f are electrically connected by the plurality of wires 8g, respectively. The plurality of wires 8g are provided at predetermined positions on the rear face of the installation face region A8a, a rear face of the side face region A8b, a rear face of the top face region A8c, and a rear face of the connection region A8d.

A first width dimension w1 of the flexible substrate 8 is set so that, in a state in which the distal end edge 8h of the flexible substrate 8 is aligned with the first short edge 2S1 of the substrate 2Aa, an opposite edge 8k that is opposite to the distal end edge 8h intersects with a midway part of the plurality of first wires 2e1 that are formed on the substrate 2Aa.

On the other hand, a width dimension (second width dimension) w2 of the proximal end edge 8j that is opposite to the distal end edge 8h of the flexible substrate 8 is set to the same dimension as the proximal end edge 6er of the top face 6e. Further, a length dimension of a first side edge 8m1 of the flexible substrate 8 is set to a dimension L that is approximately the same dimension as the length dimension of the substrate 2Aa.

The image pickup apparatus 1A of the present embodiment is assembled by the procedure described below.

When assembling the image pickup apparatus 1A, a worker prepares the solid-state image pickup device 2A, the prism 5, the holding barrel 6, the unit main body 7, and the flexible substrate 8 and the like.

Next, the worker places the installation face 6a1 of the holding barrel 6 on the installation face region A8a of the flexible substrate 8. At this time, the worker brings the distal end edge 6f of the holding barrel 6 into line with the distal end edge 8h of the flexible substrate 8 and also brings a long edge 6L2 of the holding barrel 6 into line with a second side edge 8m2 of the flexible substrate 8. Thereafter, the worker integrally fixes the flexible substrate 8 and the holding barrel 6 to each other by means of, for example, a thermosetting adhesive.

Subsequently, the worker, for example, places the rear face of the flexible substrate 8 that is integrated with the holding barrel 6 onto the terminal portion region A2d and the circuit portion region A2c of the substrate 2Aa of the solid-state image pickup device 2A. As a result, the installation face region A8a portion that is one part of the flexible substrate 8 is disposed between the front face of the substrate 2Aa and the installation face 6a1 of the holding barrel 6A. At this time, the installation face 6a1 is disposed on the terminal portion region A2d and the circuit portion region A2c on the front face of the substrate 2Aa via the flexible substrate 8.

In this case, the worker brings the distal end edge 8h of the flexible substrate 8 into line with the first short edge 2S1 of the substrate 2Aa, and brings the second side edge 8m2 of the flexible substrate 8 into line with the long edge 2L2 of the substrate 2Aa. In addition, the worker sets the plurality of electrode pads 2d and the plurality of pad connection electrodes 8e in an opposed positional relationship, and disposes gold bumps 9a that are connection members for electrically connecting the electrode pads 2d and the plurality of pad connection electrodes 8e in a predetermined state.

Thereafter, the worker integrally fixes the substrate 2Aa and the flexible substrate 8 by means of an adhesive. As a result, as shown in FIG. 6, the electrode pads 2d and the plurality of pad connection electrodes 8e are electrically connected through the gold bumps 9a. Reference character 9b denotes an adhesive layer.

Note that the above-described adhesive is, for example, a thermosetting adhesive. Further, connection members are not limited to the gold bumps 9a, and may be solder bumps or the like.

Next, as shown in FIG. 5, the worker disposes the incidence surface of the prism 5 at the proximal end face of the holding barrel 6, and integrally fixes the exit surface 5b of the prism 5 in the light-receiving portion region A2b of the substrate 2Aa of the solid-state image pickup device 2A by means of, for example, an ultraviolet-curing adhesive. As a result, the entire front face of the substrate 2Aa is supported by the holding barrel 6 of the objective lens unit 4 and the prism 5 that constitute the objective optical portion 3.

Next, the worker turns up the flexible substrate 8 that extends from the substrate 2Aa to dispose the side face region A8b of the flexible substrate 8 on the side face 6d and chamfered portion 6c1 of the holding barrel 6 and dispose the top face region A8c of the flexible substrate 8 on the top face 6e of the holding barrel 6. Thereafter, as shown in. FIG. 7, the worker integrally fixes the side face region A8b to the side face 6d and the chamfered portion 6c1 and integrally fixes the top face region A8c to the top face 6e by means of, for example, a thermosetting adhesive.

Finally, the worker inserts the unit main body 7 into the through-hole 6b of the holding barrel 6. The worker then moves the unit main body 7 back and forth in the longitudinal direction of the holding barrel 6 to perform focusing adjustment. After completing the focusing adjustment, the worker integrally fixes the unit main body 7 to the holding barrel 6 by adhesive bonding or the like. Thus, as shown in FIG. 7, the image pickup apparatus 1A is constructed in which the connection region A8d of the flexible substrate 8 protrudes to the proximal end side of the holding barrel 6.

Note that, although not illustrated in the drawings, signal wires are electrically connected to the plurality of signal-wire connection electrodes 8f, respectively. Further, the assembly procedure is not limited to the sequence described above, and can be appropriately changed in consideration of workability.

Thus, the image pickup apparatus 1A is constructed by fixing the holding barrel 6 of the objective lens unit 4 and the prism 5 constituting the objective optical portion 3 via the flexible substrate 8 to the entire front face of the substrate 2Aa constituting the solid-state image pickup device 2.

According to this configuration, the entire region of the substrate 2Aa is supported by the holding barrel 6 and the prism 5, and thus the problem of the occurrence of cracking and breakage in the solid-state image pickup device 2 can be solved. As a result, the workability of the small-size image pickup apparatus 1 is significantly enhanced and the yield thereof is significantly improved.

Further, because the flexible substrate 8 that extends from the holding barrel 6 is integrally fixed to the side face 6d, the chamfered portion 6c1, and the top face 6e of the holding barrel 6, an increase in the size of the image pickup apparatus 1A can be reliably prevented.

Note that the wiring space that is provided between the long edge 2L1 and the first edge 2b1 of the light-receiving portion 2b and between the long edge 2L2 and the second edge 2b2 of the light-receiving portion 2b of the substrate 2a of the first embodiment, is not required in the substrate 2Aa of the solid-state image pickup device 2A of the present embodiment.

Accordingly, when the light-receiving portion 2b and the circuit portion 2c that have the same shape as in the first embodiment are provided on the substrate 2Aa, the width dimension of the substrate 2Aa can be set to a dimension that is smaller by an amount corresponding to the aforementioned pair of wiring spaces relative to the width dimension of the substrate 2a. Consequently, the size of the image pickup apparatus can be further reduced.

A configuration may also be adopted in which an electrode for mounting a component is provided between the wires of the flexible substrate 8, and an electronic component such as a chip capacitor is mounted to the electrode.

The flexible substrate 8 is not limited to the above-described embodiment, and a flexible substrate 8A as shown in FIG. 8 may also be adopted.

The front face of the flexible substrate 8A shown in FIG. 8 is partitioned into an objective optical portion region A8n, the side face region A8b, the top face region A8c, and the connection region A8d. In the present embodiment, the installation face 6a1 of the holding barrel 6 as well as the exit surface 5b of the prism 5 are disposed and fixed on the objective optical portion region A8n.

Consequently, the length dimension of the objective optical portion region A8n is set to a dimension L that is approximately the same dimension as the length dimension of the substrate 2Aa. That is, the objective optical portion region A8n is configured to be disposed over the entire front face of the substrate 2Aa. Therefore, at a predetermined position of the objective optical portion region A8n, an opening 8o is formed so that the light-receiving portion 2b provided on the substrate 2Aa is left open.

In the flexible substrate 8A, the installation face region A8a of the holding barrel 6 and the exit surface 5b of the prism 5 are disposed on the front face of the objective optical portion region A8n and are each integrally fixed thereto by means of an adhesive. Reference character 9c denotes a cavity that is formed in the adhesive layer 9b.

According to this configuration, as shown in FIG. 9, the entire region of the front face of the substrate 2Aa is supported by the holding barrel 6 and the prism 5 via the flexible substrate 8A, and thus the problem of the occurrence of cracking and breakage in the solid-state image pickup device 2 can be solved.

A third embodiment of the present invention will now be described with reference to FIG. 10 to FIG. 13.

Figure 10:
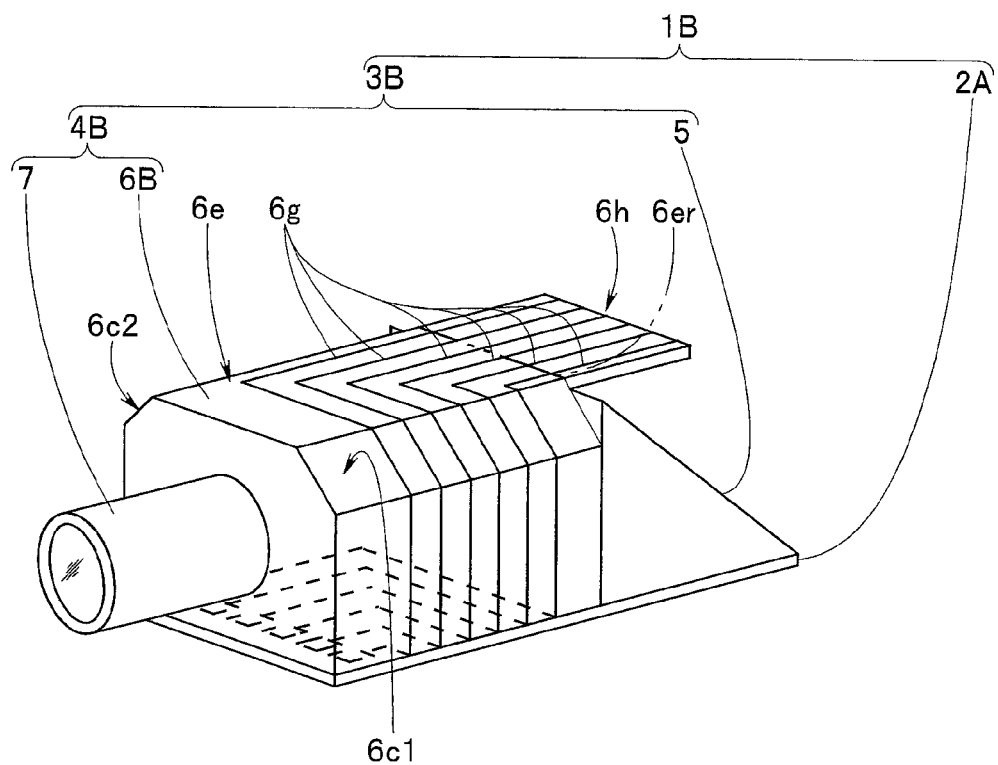
FIG. 10 is a view that illustrates an image pickup apparatus according to a third embodiment.
Figure 11:
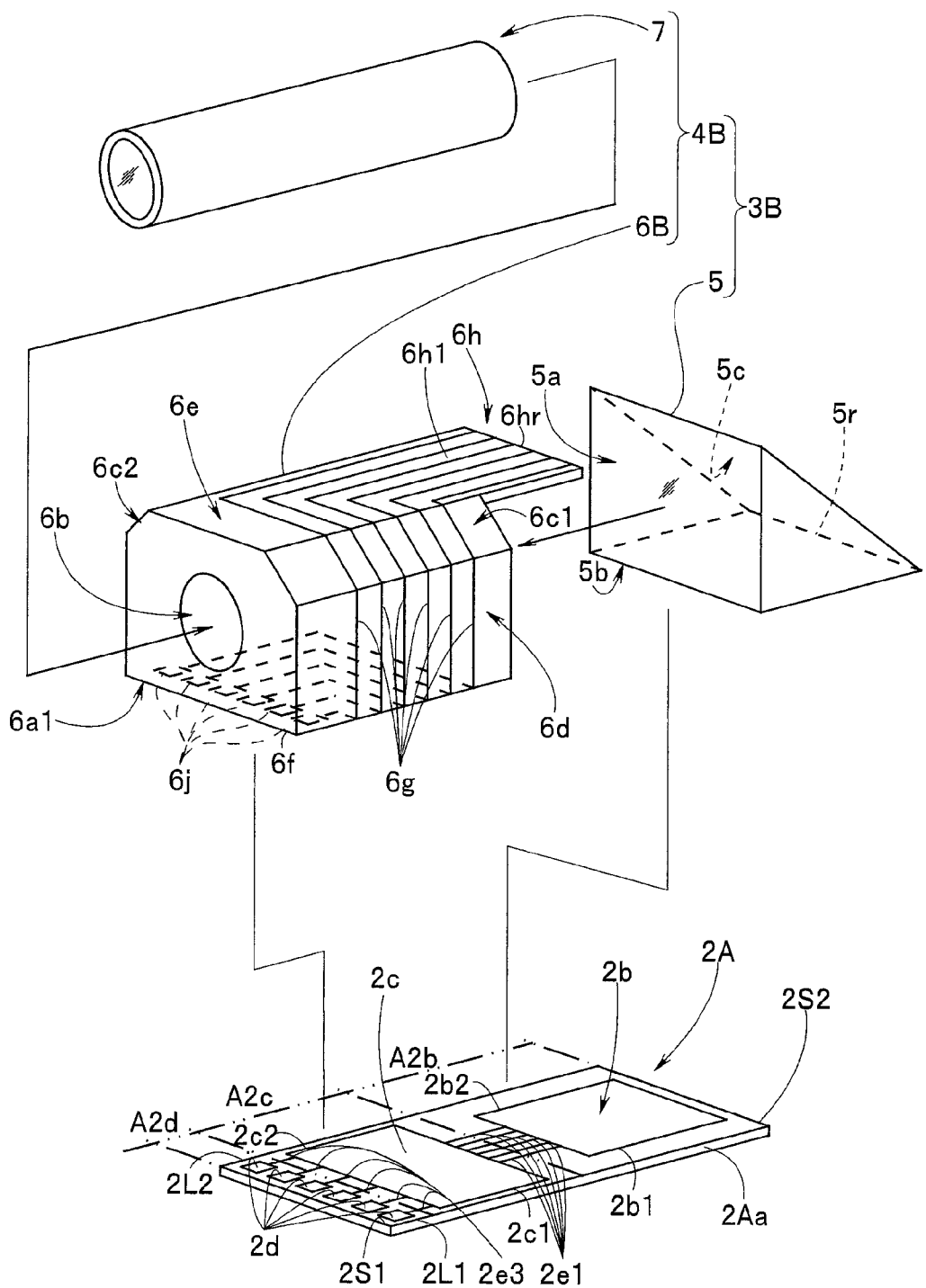
FIG. 11 is an exploded perspective view for describing the configuration of the image pickup apparatus according to the third embodiment.
Figure 12:
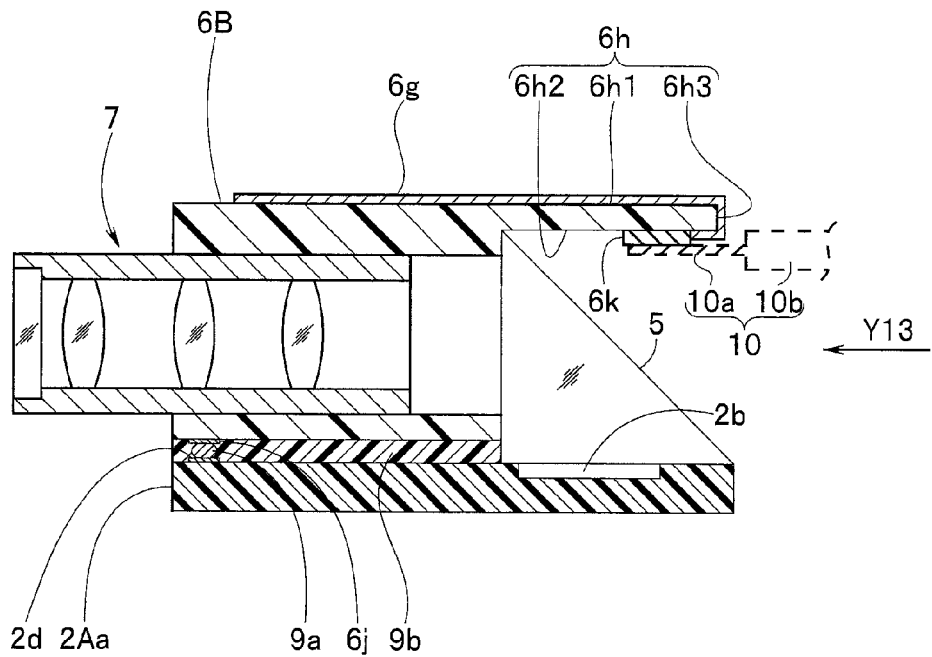
FIG. 12 is a view for describing a connection relationship between electrode pads and pad connection electrodes and a connection state between second contact points and signal wires in a state in which a holding barrel and a prism are mounted on a front face of a substrate constituting a solid-state image pickup device.
Figure 13:
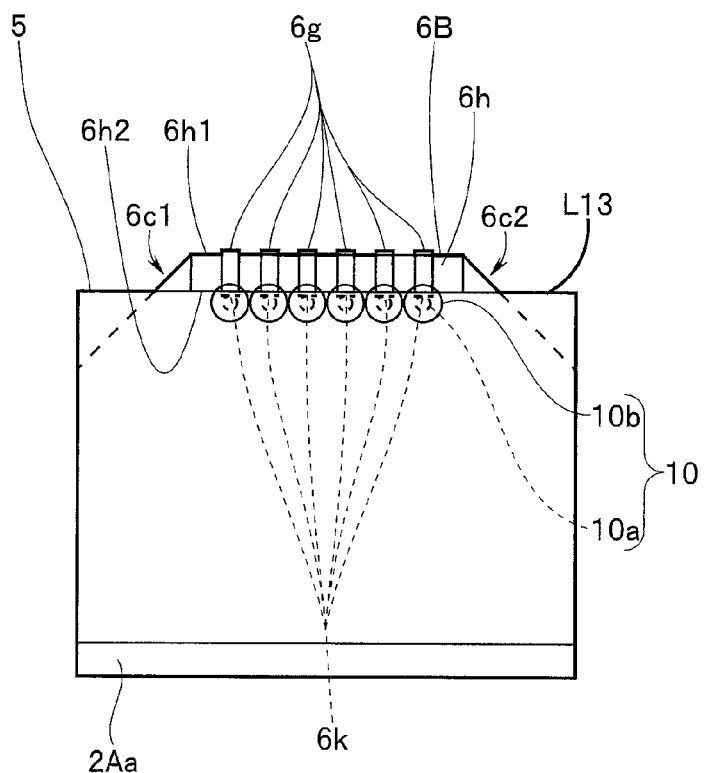
FIG. 13 is an explanatory view when the image pickup apparatus shown in FIG. 12 is seen from the side of an arrow 13.

FIG. 10 is a view that illustrates an image pickup apparatus according to the third embodiment. FIG. 11 is an exploded perspective view for describing the configuration of the image pickup apparatus according to the third embodiment. FIG. 12 is a view for describing a connection relationship between electrode pads and pad connection electrodes and a connection state between second contact points and signal wires in a state in which a holding barrel and a prism are mounted on a front face of a substrate constituting a solid-state image pickup device. FIG. 13 is an explanatory view when the image pickup apparatus shown in FIG. 12 is seen from the side of an arrow 13.

Note that in the following description of the third embodiment, components that are the same as in the above-described embodiments are denoted by the same reference characters and a description of such components is omitted.

As shown in FIG. 10, an image pickup apparatus 1B of the present embodiment includes the solid-state image pickup device 2A and an objective optical portion 3B. The objective optical portion 3B includes an objective lens unit 4B and the prism 5. The objective lens unit 4B includes a holding barrel 6B and the unit main body 7. Reference character 6g denotes three-dimensional wiring.

As shown in FIG. 10 and FIG. 11, the holding barrel 6B is a substantially rectangular parallelepiped shape and has a canopy portion 6h. The canopy portion 6h is a convex portion that protrudes by a predetermined distance in a longitudinal axis direction from the proximal end edge 6er of the top face 6e of the holding barrel 6B. A first face 6h1 of the canopy portion 6h and the top face 6e are coplanar.

The holding barrel 6B has the installation face 6a1 that is disposed on the terminal portion region A2d and the circuit portion region A2c on the front face of the substrate 2Aa. The through-hole 6b is also formed in the holding barrel 6B. Note that the holding barrel 6B is made from, for example, a resin that has light blocking properties and also has insulation properties.

Reference characters 6c1 and 6c2 denote chamfered portions and reference character 6d1 denotes a first side face.

A plurality of first contact points 6j are provided in an arrayed manner along the distal end edge 6f in a vicinity of the distal end edge 6f on the installation face 6a1 of the holding barrel 6B. The first contact points 6j are electrically connected to the plurality of electrode pads 2d provided in the terminal portion region A2d of the substrate 2Aa.

As shown in FIG. 12, a plurality of second contact points 6k are provided on a second face 6h2 of the canopy portion 6h of the holding barrel 6B. The second contact points 6k are used when inputting and outputting signals between the circuit portion 2c of the substrate 2Aa and an external apparatus through the first contact points 6j. The second face 6h2 is the face that is opposite the first face 6h1, in other words, is a rear face of the first face 6h1. The plurality of second contact points 6k are arrayed along a proximal end edge 6hr of the canopy portion 6h in a vicinity of the proximal end edge 6hr.

The three-dimensional wiring 6g is provided on the installation face 6a1, the first side face 6d1, the first chamfered portion 6c1, and the top face 6e of the holding barrel 6, on the first face 6h1 and the proximal end face 6h3 of the canopy portion 6h, and on the second face 6h2 of the canopy portion 6h. The three-dimensional wiring 6g electrically connects the plurality of first contact points 6j and the plurality of second contact points 6k.

The image pickup apparatus 1B of the present embodiment can be assembled by the procedure described below.

When assembling the image pickup apparatus 1B, a worker prepares the solid-state image pickup device 2A, the prism 5, the holding barrel 6B, and the unit main body 7 and the like.

Next, the worker, for example, places the installation face 6a1 of the holding barrel 6B on the terminal portion region A2d and on the circuit portion region A2c of the substrate 2Aa of the solid-state image pickup device 2A. In this case, the worker sets the plurality of electrode pads 2*d* and the plurality of first contact points 6*j* in an opposed positional relationship, and also disposes the gold bumps 9*a* that are connection members for electrically connecting the electrode pads 2*d* and the plurality of first contact points 6*j* in a predetermined state.

Thereafter, the worker integrally fixes the substrate 2Aa and the holding barrel 6B together by means of an adhesive. As a result, as shown in FIG. 12, the electrode pads 2*d* and the plurality of first contact points 6*j* are electrically connected via the gold bumps 9*a*. Reference character 9*b* denotes the adhesive layer. A thermosetting adhesive that has insulation properties is used as the adhesive.

Next, the worker disposes the incidence surface of the prism 5 at the proximal end face of the holding barrel 6, and integrally fixes the exit surface 5*b* of the prism 5 in the light-receiving portion region A2*b* of the substrate 2Aa of the solid-state image pickup device 2A by means of, for example, an ultraviolet-curing adhesive. As a result, the entire front face of the substrate 2Aa is supported by the holding barrel 6B of the objective lens unit 4 and the prism 5 that constitute the objective optical portion 3.

Subsequently, the worker connects core wires 10*a* of the plurality of signal wires 10 to the second contact points 6*k*, respectively.

Finally, the worker inserts the unit main body 7 into the through-hole 6*b* of the holding barrel 6, performs focusing adjustment, and thereafter adhesively fixes the unit main body 7 to the holding barrel 6.

Thus, the image pickup apparatus 1B shown in FIG. 10 is constructed.

Note that the assembly procedure is not limited to the order described above, and can be appropriately changed in consideration of workability.

By constructing the image pickup apparatus 1B in which the holding barrel 6B of the objective lens unit 4 and the prism 5 constituting the objective optical portion 3 are fixed onto the entire front face of the substrate 2Aa constituting the solid-state image pickup device 2A in this manner, the problem of the occurrence of cracking or breakage in the solid-state image pickup device 2 can be solved. Further, by providing the first contact points 6*j*, the second contact points 6*k*, and the three-dimensional wiring 6*g* that connects the first contact points 6*j* and the second contact points 6*k* in the holding barrel 6B, the flexible substrate 8 is not required, and thus the number of components can be reduced and the assembly man-hours can be decreased.

Further, by connecting the core wires 10*a* of the signal wires 10 to the second contact points 6*k* provided on the second face 6*h*2, respectively, as shown in FIG. 13, outer covers 10*b* of the signal wires 10 whose core wires 10*a* are connected to the second contact points 6*k* remain inside a side-face contour line that is indicated by an extra thick line L13 of the image pickup apparatus 1B.

Consequently, it is possible to prevent enlargement of the external shape of the image pickup apparatus 1B due to the signal wires 10 that are connected to the second contact points 6*k* being disposed further to the outside than the side-face contour line of the image pickup apparatus 1B.

Note that in the present embodiment, an electronic component such as a chip capacitor may be mounted on the second face 6*h*2 of the canopy portion 6*h*.

Furthermore, in the image pickup apparatus 1A of the second embodiment, a configuration may also be adopted in which a canopy portion is provided on the holding barrel 6, and the connection region A8*d* of the flexible substrate 8 is folded onto the second face of the canopy portion so as to dispose the signal-wire connection electrodes 8*f* on the second face. According to this configuration, by connecting the signal wires to the signal-wire connection electrodes 8*f* that were folded so as to be disposed on the second face of the canopy portion, it is possible to prevent enlargement of the external shape of the image pickup apparatus 1A due to the signal wires being disposed further to the outside than the side-face contour line of the image pickup apparatus 1A.

It should be understood that the present invention is not limited to only the above-described embodiments, and various changes and modifications thereof can be made without departing from the spirit and scope of the invention.

What is claimed is:

1. An image pickup apparatus, comprising:
    a solid-state image pickup device in which one surface of a substrate is partitioned into:
        a light-receiving portion region in which a light-receiving portion is provided that generates an image pickup signal of a picked-up optical image of a subject,
        a circuit portion region in which a circuit portion is provided that performs signal processing on the image pickup signal that is generated by the light-receiving portion and generates a driving signal that drives the light-receiving portion, and
        a terminal portion region in which a plurality of terminals are provided that are used when inputting and outputting signals between the circuit portion and an external apparatus; and
    an objective optical portion comprising:
        an objective lens unit comprising a unit main body including an objective lens group for forming an optical image of the subject and a holding barrel in which the unit main body is fixedly installed, the objective lens unit having a distal end in which input light is incident, and
        a prism that bends an optical axis of the unit main body and guides the optical image that passes through the objective lens unit to the light-receiving portion of the solid-state image pickup device, the prism being provided so as to be adjacent to the holding barrel in a proximal end direction of the objective lens unit;
    wherein, on the substrate, the circuit portion region is disposed so as to be adjacent to the light-receiving portion region on a side of the distal end on which the input light is incident relative to the light-receiving portion region,
    the holding barrel includes an inner circumferential surface for accommodating the unit main body and an outer peripheral side surface on which the circuit portion region is disposed, and
    the prism is attached to the light-receiving portion region of the substrate.

2. The image pickup apparatus according to claim 1, wherein
    in a configuration in which the circuit portion region, the light-receiving portion region, and the terminal portion region are provided in order from a distal end side of the substrate on the one surface of the substrate,
    the holding barrel is fixedly installed on the circuit portion region of the substrate, the prism of the objective optical portion is fixedly installed on the light-receiving portion region of the substrate, and the terminal portion region of the substrate is exposed to an outside.

3. The image pickup apparatus according to claim 1, wherein
in a configuration in which the terminal portion region, the circuit portion region, and the light-receiving portion region are provided in order from a distal end side of the substrate on the one surface of the substrate,
the holding barrel and/or the prism of the objective optical portion is fixedly installed on the substrate via a flexible substrate having: a plurality of first electrodes that are electrically connected to the plurality of terminals of the terminal portion region of the substrate, respectively; a plurality of second electrodes that are used when inputting and outputting signals between the circuit portion of the substrate and an external apparatus through the first electrodes; and at a predetermined position on another surface, wiring that electrically connects the first electrodes and the second electrodes.

4. The image pickup apparatus according to claim 3, wherein
the flexible substrate comprises: an installation face region having the first electrodes and the wiring on the other surface side and in which an installation face of the holding barrel is fixed on the one surface side, a side face region having the wiring on the other surface side and in which a side face of the holding barrel is fixed on the one surface side, a top face region having the wiring on the other surface side and in which a top face of the holding barrel is fixed on the one surface side, and a connection region having the wiring and the second electrodes on the other surface side; and
a rear face of the installation face region of the flexible substrate on which the holding barrel is fixed is fixed in the terminal portion region and the circuit portion region of the substrate, and an exit surface of the prism is fixed in the light-receiving portion region of the substrate to support entirely of the one surface side of the substrate by means of the objective optical portion.

5. The image pickup apparatus according to claim 3, wherein
the flexible substrate comprises: an objective optical portion region having an opening that exposes the light-receiving portion of the substrate on the one surface side and having the first electrodes and the wiring on the other surface side, and in which an installation face of the holding barrel and an exit surface of the prism are fixed on the one surface side; a side face region having the wiring on the other surface side and in which a side face of the holding barrel is fixed on the one surface side; a top face region having the wiring on the other surface side and in which a top face of the holding barrel is fixed on the one surface side; and a connection region having the wiring and the second electrodes on the other surface side, and
a rear face of the installation face region of the flexible substrate on which the holding barrel and the prism are fixed is fixed on the one surface of the substrate having the terminal portion region, the circuit portion region, and the light-receiving portion to support entirely of the one surface side of the substrate by means of the objective optical portion.

6. The image pickup apparatus according to claim 4, wherein
a convex portion having a first face that is a same face as the top face of the holding barrel and that further protrudes from a proximal end edge of the top face to a proximal end side is provided in the holding barrel, and
after one part of the connection region of the flexible substrate is disposed on the first face of the convex portion, the connection region is folded to dispose the second electrodes that are provided in the connection region on a second face that is a rear face of the first face.

7. The image pickup apparatus according to claim 5, wherein
a convex portion having a first face that is a same face as the top face of the holding barrel and that further protrudes from a proximal end edge of the top face to a proximal end side is provided in the holding barrel, and
after one part of the connection region of the flexible substrate is disposed on the first face of the convex portion, the connection region is folded to dispose the second electrodes that are provided in the connection region on a second face that is a rear face of the first face.

8. The image pickup apparatus according to claim 1, wherein
in a configuration in which the terminal portion region, the circuit portion region, and the light-receiving portion region are provided in order from a distal end side of the substrate on the one surface of the substrate,
the holding barrel comprises:
a plurality of first contact points that are provided on an installation face of the holding barrel and that are electrically connected to the plurality of terminals of the terminal portion region of the substrate, respectively,
a plurality of second contact points that are provided on a canopy portion of the holding barrel and that are used when inputting and outputting signals between the circuit portion of the substrate and an external apparatus through the first contact points, and
wiring that is provided on the installation face, a side face, a top face, and the canopy portion of the holding barrel, and that electrically connects the second contact points and the first contact points.

9. The image pickup apparatus according to claim 8, wherein
the canopy portion is a convex portion having a first face that is a same face as the top face and that protrudes from a proximal end of the top face of the holding barrel to the proximal end side, and
the plurality of second contact points are provided on the proximal end side of a second face that is a rear face of the first face of the convex portion.

* * * * *